(12) United States Patent
Maker et al.

(10) Patent No.: US 10,416,036 B2
(45) Date of Patent: Sep. 17, 2019

(54) MATURATION MONITORING APPARATUS AND METHODS

(71) Applicant: M SQUARED LASERS LIMITED, Glasgow (GB)

(72) Inventors: Gareth Thomas Maker, Strathclyde (GB); Graeme Peter Alexander Malcolm, Strathclyde (GB); John Nicholls, Strathclyde (GB)

(73) Assignee: M Squared Lasers Limited, Glasgow (GB)

( * ) Notice: Subject to any disclaimer, the term of this patent is extended or adjusted under 35 U.S.C. 154(b) by 371 days.

(21) Appl. No.: 14/892,651

(22) PCT Filed: May 21, 2014

(86) PCT No.: PCT/GB2014/051568
§ 371 (c)(1),
(2) Date: Nov. 20, 2015

(87) PCT Pub. No.: WO2014/188195
PCT Pub. Date: Nov. 27, 2014

(65) Prior Publication Data
US 2016/0097695 A1 Apr. 7, 2016

(30) Foreign Application Priority Data

May 22, 2013 (GB) .................... 1309232.5

(51) Int. Cl.
*G01M 3/04* (2006.01)
*G01N 21/85* (2006.01)
(Continued)

(52) U.S. Cl.
CPC .............. *G01M 3/04* (2013.01); *C12H 1/22* (2013.01); *G01N 21/031* (2013.01);
(Continued)

(58) Field of Classification Search
CPC ............ G01M 3/02; G01M 3/04; C12H 1/22; G01N 21/31; G01N 21/3504
(Continued)

(56) References Cited

U.S. PATENT DOCUMENTS 98,784 A    1/1870  Marland et al.
2,212,211 A * 8/1940  Pfund .................... G01N 21/05
                                                136/214

(Continued)

FOREIGN PATENT DOCUMENTS

CN      201177597 Y    1/2009
DE      44 28 915 A1   2/1996
(Continued)

OTHER PUBLICATIONS

Authors: Frank K.Tittel, Lei Dong, R. Lewicki, K.Liu, L.Gong, R.Griffin and V.Spagnolo, Title: Mid-Infrared Quantum Cascade Laser based Trace Gas Sensor technologies: Recent Advances and Applications, Date: 2011, Publisher: IEEE, pp. 3.*

(Continued)

*Primary Examiner* — Daniel S Larkin
(74) *Attorney, Agent, or Firm* — FisherBroyles, LLP

(57) ABSTRACT

An apparatus and a method monitor fluid loss from one or more casks during a maturation process. The apparatus comprises a multi-pass absorption cell arranged in fluid communication with one or more fluid conduits, a pump and a monitoring system. The pump and fluid conduits transport a fluid sample (e.g. vapor sample) from a perimeter of the one or more casks to the multi-pass absorption cell. The monitoring system detects and identifies fluid within the multi-pass absorption cell.

11 Claims, 3 Drawing Sheets

(51) Int. Cl.
  *G01N 21/59* (2006.01)
  *C12H 1/22* (2006.01)
  *G01N 21/3504* (2014.01)
  *G01N 21/03* (2006.01)
  *G01N 1/22* (2006.01)

(52) U.S. Cl.
  CPC ......... *G01N 21/3504* (2013.01); *G01N 21/59* (2013.01); *G01N 21/85* (2013.01); *G01N 2001/2229* (2013.01); *G01N 2021/8578* (2013.01)

(58) Field of Classification Search
  USPC .............................................................. 73/40
  See application file for complete search history.

(56) References Cited

U.S. PATENT DOCUMENTS

| | | | |
|---|---|---|---|
| 2,865,770 | A | 12/1958 | Nickol |
| 2,943,940 | A | 7/1960 | Wiedemann |
| 3,001,877 | A | 9/1961 | Shapiro |
| 5,473,161 | A | 12/1995 | Nix et al. |
| 5,777,735 | A * | 7/1998 | Reagen ............... G01J 3/453 356/244 |
| 6,188,475 | B1 * | 2/2001 | Inman et al. ........ G01N 21/031 356/246 |
| 7,749,446 | B2 * | 7/2010 | Peterman, Jr. ....... G01N 21/031 422/83 |
| 2007/0242275 | A1 * | 10/2007 | Spartz et al. ........ G01N 21/031 356/451 |
| 2010/0275784 | A1 | 11/2010 | Cumplido Matesanz |

FOREIGN PATENT DOCUMENTS

| | | |
|---|---|---|
| EP | 0 305 973 A1 | 3/1989 |
| EP | 0 884 584 A1 | 12/1998 |
| EP | 1 355 147 A2 | 10/2003 |
| FR | 2 571 382 A1 | 4/1986 |
| GB | 191323548 A | 12/1913 |
| GB | 391076 | 4/1933 |
| GB | 2494853 A | 3/2013 |
| WO | WO 02/068929 A2 | 9/2002 |
| WO | WO 2011/151629 A1 | 12/2011 |
| WO | WO 2012/018537 A2 | 2/2012 |
| WO | WO 2012/166984 A1 | 12/2012 |
| WO | WO 2013/008003 A1 | 1/2013 |

OTHER PUBLICATIONS

Authors: Jana Tóthová, L'udovít Žiak, Jana Sádecká, Title: Characterization and Classification of Distilled Drinks Using Total Luminescence and Synchronous Fluorescence Spectroscopy, Date: 2008, Publisher: Acta Chimica Slovaca, vol. 1, No. 1, pp. 265-275.*

* cited by examiner

MATURATION MONITORING APPARATUS AND METHODS

This application is the U.S. national phase of International Application No. PCT/GB2014/051568 filed 21 May 2014 which designated the U.S. and claims priority to GB Patent Application No. 1309232.5 filed 22 May 2013, the entire contents of each of which are hereby incorporated by reference.

The present invention relates to apparatus and methods for use in maturation processes, and in particular apparatus and methods for monitoring fluid loss from one or more casks during a maturation process.

BACKGROUND TO THE INVENTION

Scotch malt whisky production involves several stages, the most important of which is arguably the maturation process by which new-make whisky is matured for several years in wooden casks.

Whisky is typically ~60% water, ~40% ethanol (and ~0.1% other constituents), when it is casked, but during the maturation process (which typically takes ten to twenty years) a proportion of the fluid volume in the cask is lost to the atmosphere. This is affectionately referred to in the trade as the "angels' share".

The angels' share is, in Scotland, typically around 2% volume per annum. Elsewhere in the world the loss can be as high as 5% per annum. Some whisky producers may have tens of millions of whisky casks undergoing maturation at any one time so these losses are clearly significant. In fact, the angels' share is reported to cost on the order of 10-15% of the production cost.

Wines, cognacs, armagnacs, sherries, ports, whiskeys (e.g. Bourbon) and beers may also be matured in barrels (as may balsamic vinegar), and the angels' share loss problem is also known to affect these maturation processes (to lesser or greater extents). This is therefore a wide reaching problem, and a solution that at least partially solves the problem will provide major economic benefits.

Experiments have been conducted in which whisky casks have been shrink-wrapped in order to prevent such fluid loss. While fluid loss is eliminated (or significantly reduced) by such processes there is a corresponding elimination (or significant reduction) in air ingress which is believed to negatively affect the maturation process and hence the taste of the final product.

The inventors have previously developed an alternative method and apparatus to reduce fluid loss from a cask during a maturation process as described in detail within international patent application number PCT/GB2012/051621. The apparatus comprises a vessel employed to sealably enclose the cask and thus provide an expansion volume around the cask in order to provide a means for accumulating the vapour leakage. A light source and detector based monitoring system can then be employed to determine a relative transmission of the light through the expansion volume and thus provided a measure of the fluid loss from the cask.

In practice it is not always convenient, or indeed possible, to deploy the described vessels. Furthermore, once deployed the rate of fluid loss is low and so it can be a long time before sufficient fluid loss has accumulated within the expansion volume in order to be detected by the monitoring system. These issues are particularly true for vessels designed to accommodate multiple casks.

It is recognised in the present invention that considerable advantage is to be gained in the provision of an apparatus and method capable of quickly and accurately monitoring the lost volume of product from a maturation process.

It is therefore an object of an aspect of the present invention to obviate or at least mitigate the foregoing disadvantages of the maturation monitoring apparatus and methods known in the art.

SUMMARY OF THE INVENTION

According to a first aspect of the invention, there is provided an apparatus to monitor fluid loss from one or more casks during a maturation process, the apparatus comprising a multi-pass absorption cell arranged in fluid communication with one or more fluid conduits and a pump and a monitoring system arranged to monitor fluid within the multi-pass absorption cell.

The pump and fluid conduits can be employed to provide the multi-pass absorption cell with a vapour sample which can then be monitored by the monitoring system. This results in an apparatus that is more portable, exhibits reduced operating times and greater sensitivity than those systems known in the art.

Most preferably the multi-pass absorption cell comprises a Herriot cell. Alternatively, the multi-pass absorption cell comprises a White cell. In a further alternative the multi-pass absorption cell comprises a Pfund cell.

The monitoring system may comprise a light source and a detector wherein the detector is arranged to receive light emitted from the light source following its propagation through the multi-pass absorption cell.

Optionally the light source comprises a mid-infrared laser source.

The apparatus may further comprise a purge source arranged in fluid communication with the multi-pass absorption cell.

According to a second aspect of the present invention there is provided a method of monitoring a fluid loss from one or more casks during a maturation process the method comprising:

providing a multi-pass absorption cell with a fluid sample taken from around the perimeter of the one or more casks; and monitoring a light field following its propagation through the multi-pass absorption cell.

The provision of the multi-pass absorption cell with a fluid sample may comprise pumping a vapour from around the perimeter of the one or more casks into the multi-pass absorption cell.

The monitoring of the light field following its propagation through the multi-pass absorption cell may comprise measuring the absorption or power of a light field generated by a light source.

The method may further comprise purging the multi-pass absorption cell with an inert gas.

Embodiments of the second aspect of the invention may include one or more features corresponding to features of the first aspect of the invention or its embodiments, or vice versa.

According to a third aspect of the present invention there is provided an apparatus to monitor fluid loss from one or more casks during a maturation process, the apparatus comprising a multi-pass absorption cell in fluid communication with one or more fluid conduits and a pump, the pump providing a means for drawing a fluid sample from a distal end of the one or more fluid conduits into the multi-pass absorption cell, wherein the apparatus further comprises a monitoring system to monitor the fluid sample within the multi-pass absorption cell.

BRIEF DESCRIPTION OF THE DRAWINGS

There will now be described, by way of example only, various embodiments of the invention with reference to the drawings, of which.

Figure 1:
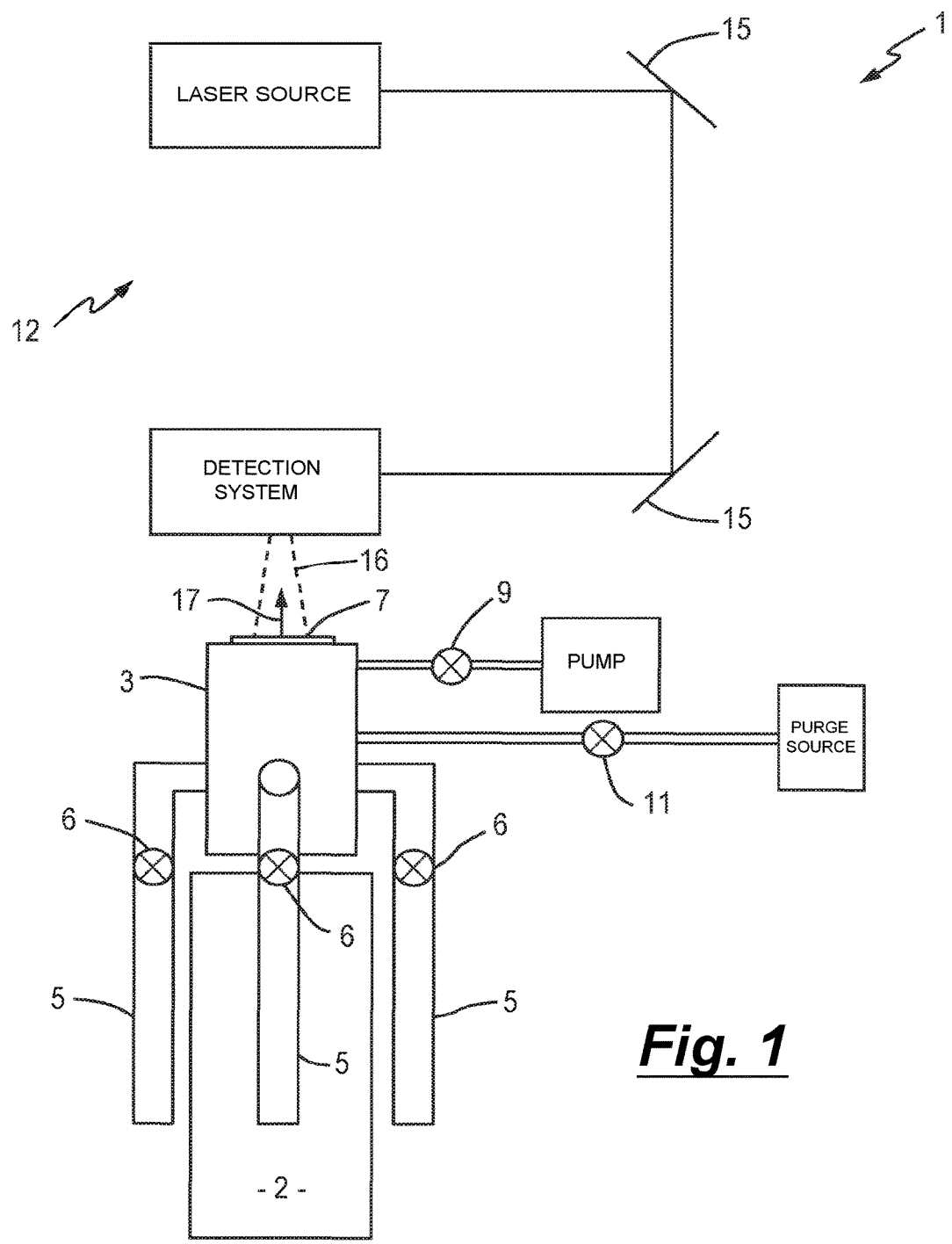
FIG. 1 illustrates in schematic form an apparatus to monitor a whisky maturation process in accordance with an aspect of the present invention.

In the description which follows, like parts are marked throughout the specification and drawings with the same reference numerals. The drawings are not necessarily to scale and the proportions of certain parts have been exaggerated to better illustrate details and features of embodiments of the invention.

DETAILED DESCRIPTION OF PREFERRED EMBODIMENTS

The following example is described in the context of the maturation of whisky within a whisky cask, however it will be understood that the invention finds utility in other maturation processes; for example of wine, cognac, armagnac, sherry, port, whiskey (e.g. Bourbon), beer and balsamic vinegar. Furthermore, while wooden casks are typically employed it is understood that casks made from other materials (such as plastics or metals as increasingly used in wine maturation or clay pots as used in the maturation of Chinese white spirits) shall not fall outside the scope of protection set out herein.

FIG. 1 presents a schematic representation of an apparatus 1 to monitor fluid loss from a cask 2 during a maturation process. The whisky cask 2 is shown sitting vertically, however it will be understood that the cask 2 may sit horizontally or at any other orientation and exhibit a regular or irregular shape.

The apparatus 1 can be seen to comprise a housing 3 within which is located a multi-pass absorption cell 4, further details of which will be described below with reference to FIG. 2. Depending from the housing 3 are four fluid conduits 5 (only three of which can be seen in FIG. 1). Valves 6 located within each of the fluid conduits provide a means for isolating the fluid conduits 5 and the multi-pass absorption cell 4.

An aperture 7 allows for light to enter and exit the housing 3. The aperture 7 is sealed by way of calcium fluoride ($CaF_2$) windows affixed thereto, although any suitable material for the windows may be used.

A pump 8 is arranged in fluid communication with the multi-pass absorption cell 4. A valve 9 provides a means for isolating the pump 8 and the multi-pass absorption cell 4. In the presently described embodiment the pump 8 and valve 9 are shown to be external to the housing 3.

A purge source 10 e.g. nitrogen or other inert gas, is also arranged to be in fluid communication with the multi-pass absorption cell 4. A valve 11 provides a means for isolating the purge source 10 and the multi-pass absorption cell 4.

The apparatus 1 can be seen to further comprise a monitoring system 12 arranged to monitor the presence of a fluid (e.g. a vapour) within the multi-pass absorption cell 4. The monitoring system comprises a mid-infrared laser source 13 and a detection system 14 both of which will be discussed in further detail below. Beam steering mirrors 15 provide a means for directing light exiting the laser source 13 via the detection system 14 so as to provide an input light 16 for the multi-pass absorption cell 4. The detection system 14 is arranged to analyse the input light 16 once it has propagated through the multi-pass absorption cell 4, referred to hereinafter as the output light 17.

Figure 2:
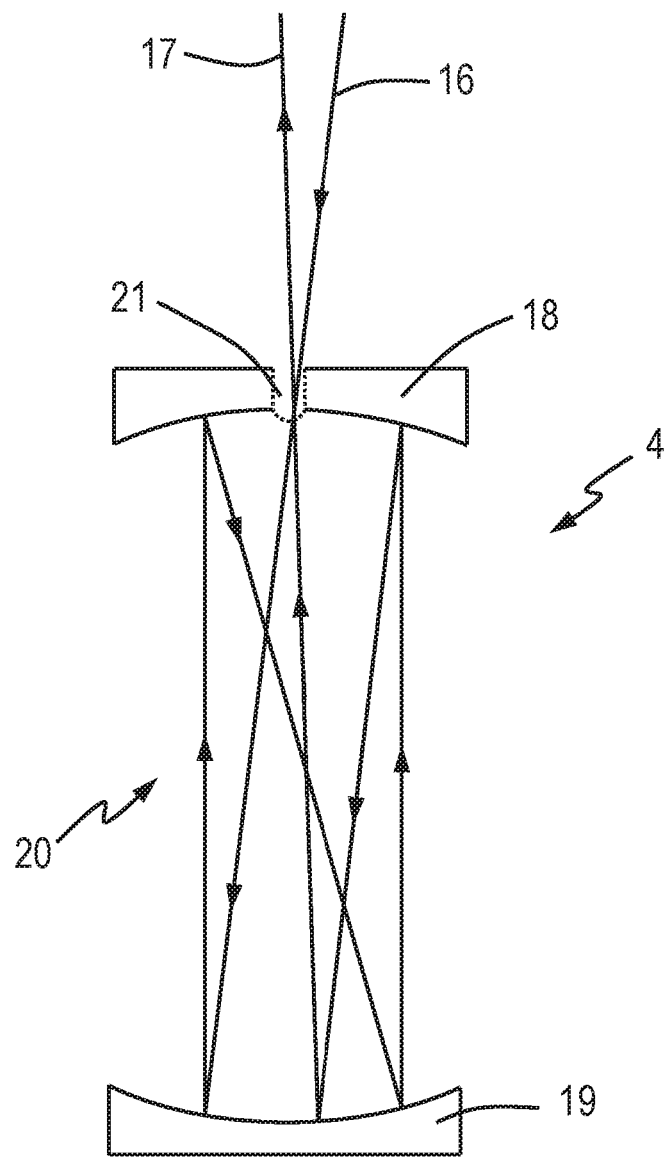
FIG. 2 presents a schematic representation of a Herriot cell employed by the apparatus of FIG. 1.

From FIG. 2 the multi-pass absorption cell 4 can be seen to comprise a Herriot cell. The Herriot cell is made up of two opposing spherical mirrors 18 and 19 arranged to form an optical cavity 20. An aperture 21 is formed within the first spherical mirror to allow the input 16 and output light 17 to enter and exit the optical cavity 20. As a result the multi-pass absorption cell 4 provides a means to improve detection sensitivity by increasing the total optical path length of the input beam 16 within a sample volume contained within the cavity 20. This results in a greater detection sensitivity for the apparatus 1, as discussed in further detail below. The number of traversals of the input beam 16, and hence the sensitivity of the apparatus 1, can be controlled by simply adjusting the separation distance between the spherical mirrors 18 and 19.

A suitable mid-infrared laser source 13 is an intracavity Optical Parametric Oscillator (OPO) as described in detail within international patent publication number WO 2006/061567. The described OPO provides a portable laser source that exhibits a pulsed output field having an output power of around 70 mW, a pulse repetition frequency of more than 100 kHz, a spectral linewidth of less than or equal to 5 GHz and which can be wavelength tuned from 2 to 6 microns. The intracavity OPO 13 is therefore an ideal source for carrying out absorption spectroscopy upon a fluid leaking from the cask 2 since an output wavelength of 3306 nm coincides with the O—H and C—H stretch absorption bands of ethanol. Accordingly transmission through the multi-pass absorption cell 4 gives an indication of the presence of ethanol within the cell 4.

A suitable detection system 14 is a raster scanning and detection system as also described in detail within international patent publication number WO 2006/061567. This system is capable of collecting, recording and analysing the back-scattered absorption signal 17 returning from the multi-pass absorption cell 4 so allowing the power of the output light 17 to be recorded as a function of time.

In an alternative embodiment the detection system 14 may comprise a laser power meter, connected to a data logger, for example a PC with a suitable data acquisition card, so as to again enable the recording of the power of the output light 17 as a function of time.

It will be further appreciated that alternative multi-pass absorption cells 4 may be employed with the apparatus. For example the Herriott cell may be one that operates in transmission i.e. the second spherical mirror comprises an aperture and the laser source 13 and detection system 14 are located on opposite sides of the cell. Alternatively, the multi-pass absorption cell 4 may comprise a White cell or a Pfund cell, as are known in the art.

In the above described embodiment the pump 8; valves 6, 9 and 11; purge source 10, laser source 13, detection system 14 and beam steering mirrors 15 are all shown to be external to the housing 3. It will be appreciated that in alternative embodiments one or more of these components may be located within the housing 3 itself.

Method for Monitoring Fluid Loss

Figure 3:
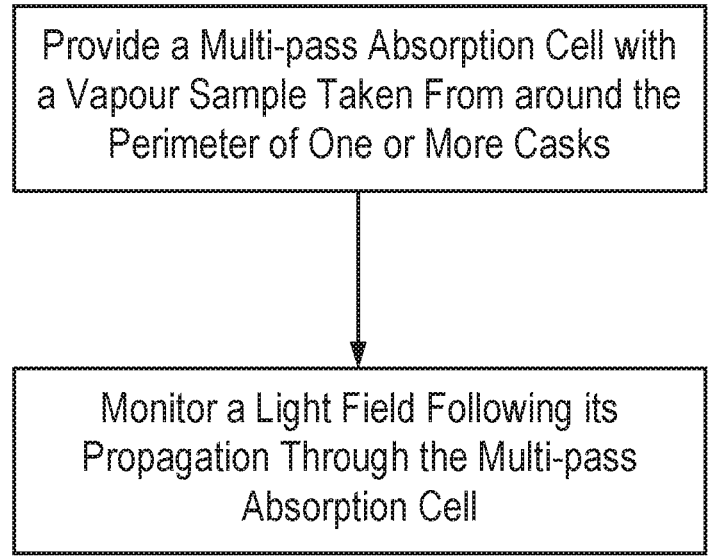
FIG. 3 presents a flow chart of the methodology involved in monitoring a whisky maturation process.

The method for monitoring fluid loss from the cask 2 will now be described with reference to FIG. 3.

Initially the multi-pass absorption cell is provided with vapour sample taken from around the perimeter of one or more casks. This is achieved by locating the apparatus in fluid communication with outer surface of a cask to be monitored. In practice this is achieved by locating the distal ends of the fluid conduits around the perimeter of the cask. A sample of the air is then drawn into the optical cavity of the multi-pass absorption cell 4. This is achieved by operating the pump 8 with the pump valve 9 and the fluid conduit valves 6 in their open position.

The mid-infrared laser source 13 and a detection system 14 are then employed so as to monitor the input light 16 following its propagation through the multi-pass absorption cell 4 e.g. by measuring the absorption or power of the light generated by the laser source 13. This may be carried out with the pump valve 9 and the fluid conduit valves 6 in their open positions i.e. with a constant flow or air through the multi-pass absorption cell 4. Alternatively, these valves 6 and 9 may be closed after a predetermined time such that the power recording may be taken on a fixed sample.

It is preferable to purge the multi-pass absorption cell 4 prior to taking a power recording. This could be achieved by moving the distal ends of the fluid conduits 5 away from the cask 2 and then running the pump 8 with the pump valve 9 and the fluid conduit valves 6 in their open positions. However, it is not always possible to simply move the distal ends of the fluid conduits 5 into an environment where the operator can be confident that there is no "angel share". This is particularly true when carrying out tests at whisky distillery or similar location where whisky casks are stored. The preferable option for purging the multi-pass absorption cell 4 is to open the fluid conduit valves 6, the pump valve 9 and the purge source valve 11 such that nitrogen gas flows through the apparatus 1.

Although the above apparatus and methods have been described with respect to a single cask 2 it will be appreciated that the apparatus may be deployed with two or more casks as defined be the location of the distal ends of the fluid conduits 5.

It will be appreciated that the number of fluid conduits 5 is not restricted to four, as described in the above embodiments. The apparatus would function as previously described with the use of a single fluid conduit 5.

While the exemplary embodiment has been described as monitoring the presence of ethanol within the vessel volume using laser source 13 and detection system 14 other useful information may be gleaned by employing a spectrometer or spectrophotometer to analyse the atmospheric composition within the multi-pass absorption cell 4. The spectrometer may be of any suitable kind, for example a tuneable diode laser absorption spectrometer or an active infrared hyperspectral imaging system such as described in international patent publication number WO 2006/061567. Thus, a detailed analysis of the composition of the atmosphere within the multi-pass absorption cell 4 might be determined in real-time.

The above described apparatus and methods provide a means for monitoring the level of ethanol vapour leaking from one or more casks. Optionally, the atmospheric composition can also be determined. Furthermore, the apparatus is significantly more portable than those systems known in the art while exhibiting reduced operating times and greater sensitivity.

The invention provides an apparatus and a method to monitor fluid loss from one or more casks during a maturation process. The apparatus comprises a multi-pass absorption cell arranged in fluid communication with one or more fluid conduits and a pump, and a monitoring system. The pump and fluid conduits provide a means for transporting a fluid sample (e.g. a vapour sample) to the multi-pass absorption cell. The monitoring system provides a means for detecting and identifying the fluid within the multi-pass absorption cell. The described apparatus is more portable, exhibits reduced operating times and greater sensitivity than those systems known in the art.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

Furthermore, reference to any prior art in the description should not be taken as an indication that the prior art forms part of the common general knowledge.

The foregoing description of the invention has been presented for purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention as defined by the appended claims.

The invention claimed is:

1. An apparatus to monitor fluid loss from a cask during a maturation process, the apparatus comprising a multi-pass absorption cell in fluid communication with two or more fluid conduits and a pump, distal ends of the two or more fluid conduits arranged around a perimeter of a single cask, the pump providing a means for drawing fluid samples from two or more discrete locations around the perimeter of the cask via the two or more fluid conduits into the multi-pass absorption cell, wherein the apparatus further comprises a monitoring system to monitor the fluid sample within the multi-pass absorption cell.

2. An apparatus as claimed in claim 1 wherein the multi-pass absorption cell comprises a Herriot cell.

3. An apparatus as claimed in claim 1 wherein the multi-pass absorption cell comprises a White cell.

4. An apparatus as claimed in claim 1 wherein the multi-pass absorption cell comprises a Pfund cell.

5. An apparatus as claimed in claim 1 wherein the monitoring system comprises a light source and a detector wherein the detector is arranged to receive light emitted from the light source following the light's propagation through the multi-pass absorption cell.

6. An apparatus as claimed in claim 5 wherein the light source comprises a mid-infrared laser source.

7. An apparatus as claimed in claim 1 wherein the apparatus further comprises a purge source arranged in fluid communication with the multi-pass absorption cell.

8. A method of monitoring a fluid loss from a cask during a maturation process the method comprising:
 providing a multi-pass absorption cell with vapour samples taken from two or more discrete locations around a perimeter of the cask; and monitoring a light field following light's propagation through the multi-pass absorption cell.

9. A method of monitoring a fluid loss from a cask as claimed in claim 8 wherein the provision of the multi-pass absorption cell with a fluid sample comprises pumping a vapour from two or more discrete locations around the perimeter of the cask into the multi-pass absorption cell.

10. A method of monitoring a fluid loss from a cask as claimed in claim 8 wherein the monitoring of the light field following the light's propagation through the multi-pass absorption cell comprises measuring the absorption or power of a light field generated by a light source.

11. A method of monitoring a fluid loss from a cask as claimed in claim 8 wherein the method further comprises purging the multi-pass absorption cell with an inert gas.

* * * * *